United States Patent [19]

Prugh

[11] 3,981,876
[45] Sept. 21, 1976

[54] 1-ALKYL-4-(10[1-PIPERIDYL]-5H-DIBENZO-[A,D]CYCLOHEPTEN-5-YLIDENE)PIPERIDINE COMPOUNDS

[75] Inventor: John D. Prugh, Lansdale, Pa.

[73] Assignee: Merck & Co., Inc., Rahway, N.J.

[22] Filed: Aug. 14, 1972

[21] Appl. No.: 280,697

Related U.S. Application Data

[63] Continuation of Ser. No. 9,049, Feb. 5, 1970, abandoned.

[52] U.S. Cl. ............................. 260/293.62; 424/267
[51] Int. Cl.² ....................................... C07D 211/28
[58] Field of Search ............................... 260/293.62

[56] References Cited
UNITED STATES PATENTS 3,014,911  12/1961  Engelhardt..................... 260/293.62

OTHER PUBLICATIONS

Neth. Patent 68, 10177 (Feb. 5, 1969) Derwent Basic 36115 pp. 557–565.

Primary Examiner—Sherman D. Winters
Attorney, Agent, or Firm—Harry E. Westlake, Jr.; Thomas E. Arther

[57] ABSTRACT

The new 1-alkyl-4-(10-oxo or -hydroxy-10,11-dihydro-5H-dibenzo[a,d]cyclohepten-5-ylidene)-piperidine compounds are prepared from the corresponding 10-desoxy compounds having a double bond at the 10,11-position by a process involving bromination, dehydrobomination of the resulting dibromo compound, followed by enamine formation and hydrolysis to give the desired 10-oxo compound. The compounds prepared in this manner are active as antihistamines and as appetite stimulants.

2 Claims, No Drawings

1-ALKYL-4-(10[1-PIPERIDYL]-5H-DIBENZO-[A,D-]CYCLOHEPTEN-5-YLIDENE)PIPERIDINE COMPOUNDS

This is a continuation of application Ser. No. 9,049 filed Feb. 5, 1970, now abandoned.

SUMMARY

This invention concerns 10-oxo or -hydroxy-10,11-dihydro-5H-dibenzo[a,d]cyclohepten-5-ylidene)-piperidine compounds, acid addition salts thereof, and processes for the preparation of said compounds from the corresponding 10-desoxy compounds. It also concerns pharmaceutical compositions in which said 10-oxo or -hydroxy compounds are incorporated as the active medicinal agent. The invention is also concerned with the use of such compounds in the treatment of certain allergic conditions and as appetite stimulants.

BACKGROUND

Allergic conditions in the past have been treated with a variety of drugs including those characterized as 1-alkyl-4-(5H-dibenzo[a,d]cyclohepten-5-ylidene)-piperidines.

Prior to the present invention, it was known that the compound cyproheptadine of the structure

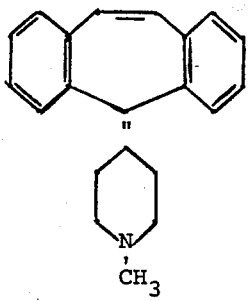

was an active antihistaminic and antiserotonin agent and was therefore useful in the treatment or relief of certain allergic conditions. This is disclosed in U.S. Pat. No. 3,014,911, E. L. Engelhardt, which patent was issued Dec. 26, 1961.

The novel 10-oxo or -hydroxy compounds of my invention are distinguished from the prior art patented compounds by their enhanced antihistaminic activity and their diminished activity with respect to serotonin antagonism and central and peripheral anticholinergic activity as measured in standard laboratory test animals.

DESCRIPTION AND PREFERRED EMBODIMENTS

The present invention relates to derivatives of 1-alkyl-4-(10,11-dihydro-5H-dibenzo[a,d]cyclohepten-5-ylidene)piperidine which are useful as drugs for the treatment of allergic conditions in humans and in particular it relates to derivatives of the following structure

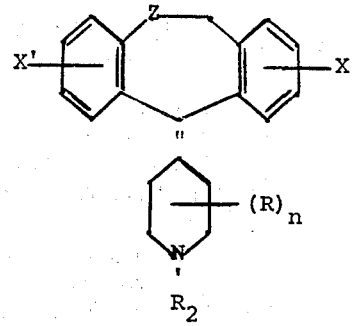

wherein $R_2$ is loweralkyl or loweralkenyl preferably containing from 1 to 6 carbon atoms; X and X' are similar or dissimilar and are selected from hydrogen, an alkyl group having up to 6 carbon atoms, a perfluoroalkyl group having up to 4 carbon atoms, a phenyl or a substituted phenyl radical, an acyl group having up to 4 carbon atoms, a perfluoroacyl group having up to 4 carbon atoms, amino, an alkylamino group having up to 4 carbon atoms, a dialkylamino group having up to 8 carbon atoms, an acylamino group have up to 4 carbon atoms, a perfluoroacylamino group having up to 4 carbon atoms, an alkylsulfonylamino group having up to 4 carbon atoms, halogen (fluorine, chlorine, bromine or iodine), hydroxyl, an alkoxyl group having up to 4 carbon atoms, a perfluoroalkoxyl group having up to 4 carbon atoms, cyano, carboxy, carbamoyl, formyl, an alkylcarbamoyl group having up to 5 carbon atoms, a dialkylcarbamoyl group having up to 9 carbon atoms, a carbalkoxy group having up to 6 carbon atoms, mercapto, an alkylmercapto group having up to 4 carbon atoms, an aralkylmercapto group especially benzylmercapto, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, a dialkylsulfamoyl group having up to 8 carbon atoms, or an alkylsulfinyl group having up to four carbon atoms; R is methyl or ethyl and may replace one or more of the hydrogens in positions 2, 3, 5 or 6 of the pyridine ring, provided that only one of positions 3 or 5 is mono-substituted at one time; n is 1 or 2; and Z is either >C=O or

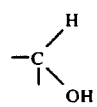

i.e., carbonyl or hydroxymethylene.

The invention also includes salts of the above compounds such as acid addition salts which may interchangeably be used in therapeutic applications with the base and likewise includes N-oxide derivatives thereof.

The invention also includes the administration of 1-alkyl-4-(10,11-dihydro-10-oxo or 10-hydroxy-5H-dibenzo[a,d]cyclohepten-5-ylidene)piperidine or an acid addition salt thereof as a treatment of allergic disorders. The treatment involves preferably the oral administration of an effective amount of the selected 1-alkyl-4-(10,11-dihydro-10-oxo-dibenzo[a,d]cyclohepten-5-ylidene)piperidine at a dosage level which will afford relief from the allergic condition.

The invention also includes a method of stimulating appetite in human patients who may be underweight or malnourished. The method employed for stimulating appetite involves the administration either orally or parenterally but preferably orally of an effective amount of a selected 1-alkyl-4-(10,11-dihydro-10-oxo- or 10-hydroxy-dibenzo[a,d]cyclohepten-5-ylidene)-piperidine.

The compounds of my invention may be administered to persons in any of the usual pharmaceutical oral forms such as tablets, elixirs and aqueous suspensions in an amount from 0.10 up to 50 mgs. per dose given 2 to 4 times daily. Sterile solutions for injection containing from 0.001 to about 25 mgs. per dose are injected 2 to 4 times a day. Further, the compounds of my invention are ordinarily easily administered as a salt and any convenient non-toxic acid addition salt formed in a conventional manner may be employed. As examples of the salts convenient for use are salts of the compounds of my invention with hydrochloric acid, sulfuric acid, phosphoric acid, acetic acid, propionic acid, citric acid, tartaric acid, succinic acid, maleic acid and the like. These salts are generally equivalent in potency to the bases from which they are formed taking into consideration the stoichiometric quantities employed.

The compounds of my invention are conveniently prepared from the compounds disclosed in the Engelhardt patent, U.S. Pat. No. 3,014,911, or from appropriately substituted 5H-dibenzo[a,d]cycloheptenones, in the manner described in column 3 of that patent, the 5H-dibenzo[a,d]cyclohepten-5-one or a derivative containing an X and/or X' substituent in the benzene rings is treated with a Grignard reagent prepared from a 1-alkyl-4-halo-piperidine or a ring alkylated 1-alkyl-4-halo-piperidine to form an intermediate carbinol, a 5-hydroxy-5-(1-alkyl-4-piperidyl)-5H-dibenzo[a,d]cycloheptene which is then dehydrated to produce the desired starting material, a 1-alkyl-4-(5H-dibenzo[a,d]cyclohepten-5-ylidene)piperidine.

The starting material employed in the process of my invention, preferably in the form of its hydrobromide salt, is then treated with bromine to produce the corresponding 10,11-dibromo-10,11-dihydro-dibenzocycloheptene preferably isolated as the hydrobromide and subsequently the dibromo compound is treated with a strong base to form a mono-bromo 5H-dibenzo[a,d]cycloheptene compound which mono-bromo compound is then contacted with a piperidine or pyrrolidine in the presence of a strong base to produce a 10-enamine derivative. The resulting 10-enamine derivative is then hydrolyzed to produce a biologically active 10-keto compound which is readily reduced in known manner to the corresponding 10-hydroxy compound which also is a pharmacologically active compound of the present invention. These 10-keto or 10-hydroxy compounds, in addition to their biological activity, are also useful as intermediates in the preparation of other active dibenzocycloheptene compounds in which the 10-oxygen function is replaced by other functional substituents using readily available synthetic methods.

The process for the preparation of the compounds of my invention is conveniently illustrated by the following process outline:

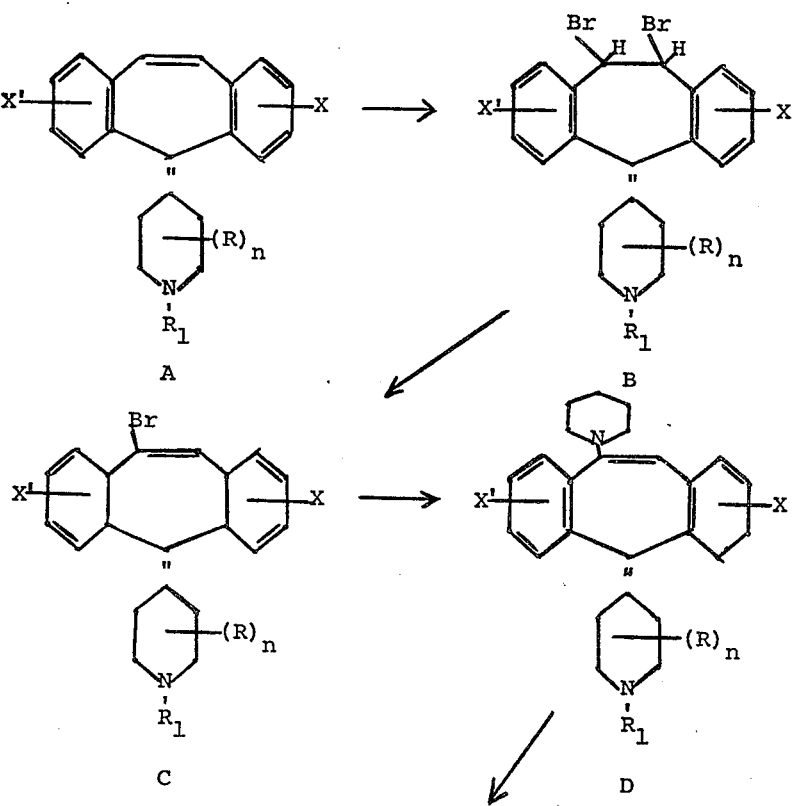

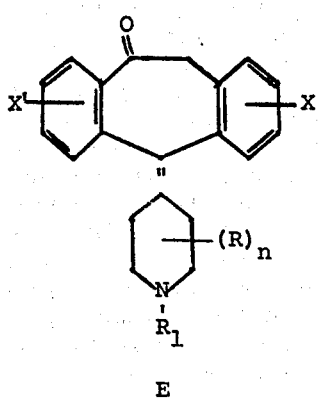

E wherein $R_1$ is lower alkyl preferably containing from 1 to 6 carbon atoms; X and X' are similar or dissimilar and are selected from hydrogen, an alkyl group having up to 6 carbon atoms, a perfluoroalkyl group having up to 4 carbon atoms, a phenyl or a substituted phenyl radical, an acyl group having up to 4 carbon atoms, a perfluoroacyl group having up to 4 carbon atoms, amino, an alkylamino group having up to 4 carbon atoms, a dialkylamino group having up to 8 carbon atoms, an acylamino group having up to 4 carbon atoms, a perfluoroacylamino group having up to 4 carbon atoms, an alkylsulfonylamino group having up to 4 carbon atoms, halogen (fluorine, chlorine, bromine or iodine), hydroxyl, an alkoxyl group having up to 4 carbon atoms, a perfluoroalkoxyl group having up to 4 carbon atoms, cyano, carboxy, carbamoyl, an alkylcarbamoyl group having up to 5 carbon atoms, a dialkylcarbamoyl group having up to 9 carbon atoms, a carbalkoxy group having up to 6 carbon atoms, an alkylmercapto group having up to 4 carbon atoms, a perfluoroalkylmercapto group having up to 4 carbon atoms, an alkylsulfonyl group having up to 4 carbon atoms, a perfluoroalkylsulfonyl group having up to 4 carbon atoms, sulfamoyl, an alkylsulfamoyl group having up to 4 carbon atoms, or a dialkylsulfamoyl group having up to 8 carbon atoms; R is methyl or ethyl and may replace one or more of the hydrogens in positions 2, 3, 5 or 6 of the pyridine ring, provided that only one of positions 3 or 5 is mono-substituted at one time; n is 1 or 2.

In the conversion of compound B to compound C wherein the starting compound is unsymmetrically substituted, e.g., X and X' are different groups the product produced is a mixture of position isomers which differ in that the bromine substituent is present at either the 10- or 11-position. This mixture is separated by conventional methods such as chromatography and crystallization to produce the respective 10-bromo or 11-bromo position isomers of Compound C. Each of these isomers, but preferably the mixture without further crystallization, is converted to the corresponding compound D. This reaction is conducted by treatment of the mono-bromo derivative C with a strong base in the presence of piperidine to form the corresponding enamine compound D. In this instance, as in the formation of the mono-bromo compound, the reaction gives rise in the case of the unsymmetrically substituted compounds to position isomers in which the N-piperidyl substituent in the isomer is present either in the 10- or 11-position. These position isomers are separated by conventional means such as by chromatography and/or crystallization. Preferably, the mixture of isomers, but alternatively either of the position isomers, is then converted to the corresponding 10-keto, 11-keto, or a mixture of the two isomeric compounds. This mixture of 10- and 11-keto compounds is also readily separated into the component isomers by conventional techniques such as by chromatography and/or crystallization.

It will be apparent to one skilled in the art that the compounds of my invention which are unsymmetrically substituted are usually obtained as a mixture of isomers. These isomers, i.e., the geometrical, stereo and-/or the optical isomers, can be separated at any desired stage of the process. In addition, the mixtures of isomers formed are readily subjected to the various processing steps with consequent production of a mixture of isomers of the final product which in turn may be readily separated by known means. The isomers of the product of my invention when isolated in their pure form may differ in biological activity.

The process outlined in the above flowsheet is a method of introducing a 10-oxygen substituent into compound A, i.e., 1-alkyl-4-(5H-dibenzo[a,d]cyclohepten-5-ylidene)piperidine by the process of bromination, dehydrobromination, enamine formation and hydrolysis. This process is also applicable to the derivatives indicated in which the benzene rings are substituted by one or more of the named substituents.

The first step of the process, the conversion of compound A to B, is accomplished by dissolving compound A, preferably in the form of its hydrobromide salt, in a solvent for bromination as, for example, glacial acetic acid or other solvent inert to the action of bromine and adding an equivalent amount of bromine (approximately 1 mol of bromine per mol of starting compound) to the reaction to form the corresponding 1-alkyl-4-(10,11-dibromo-10,11-dihydro-5H-dibenzo[a,d]cyclohepten-5-ylidene)piperidine, compound B. The bromination is preferably conducted at room temperature 25°C. However, if it is desired, the reaction can be carried out at any temperature between 0° and 100°C. The dibromo compound is recovered by filtration and the excess solvent is removed in conventional manner.

The dibromo compound obtained is then dehydrobrominated by treatment with a strong base to produce the corresponding mono-bromo unsaturated derivative, i.e., the 1-alkyl-4-(10-bromo-5H-dibenzo[a,d]cyclohepten-5-ylidene)piperidine. In effecting this dehydrobromination, the dibromo compound is dissolved or suspended in a lower alkanol containing an excess amount of a strong base. A preferable reaction mixture is one which employs potassium-t-butoxide dissolved in t-butanol. Other mixtures which may be employed are alkali metal alcoholates dissolved in lower alkanol or alcoholic solutions of alkali metal hydroxides as, for example, sodium methoxide, sodium ethoxide, sodium propoxide, sodium-i-propoxide, potassium-i-butoxide, potassium methoxide, potassium ethoxide, potassium propoxide, and the like dissolved in methanol, ethanol, propanol, i-propanol, butanol, and/or t-butanol. The reaction is conveniently carried out by stirring vigorously a mixture of the strong base in alcohol and the dibromo compound for a period of from ½ to 24 hours at temperatures ranging from about 0° to 40°C. The unsaturated mono-bromo product obtained is isolated by pouring the reaction mixture into excess water and extracting with an aromatic hydrocarbon such as benzene. The product is recovered from the extract by removal of the benzene solvent under reduced pressure and crystallizing the product from a convenient solvent such as an aliphatic hydrocarbon fraction.

The unsaturated mono-bromo derivative (C) is then treated with a solution of a strong base in the presence of piperidine or pyrrolidine to form the corresponding enamine compound (D), i.e., the 1-alkyl-4-(10-[1-piperidyl]-5H-dibenzo[a,d]cyclohepten-5-ylidene)-piperidine. This conversion is carried out by mixing the unsaturated mono-bromo compound C and a strong base and piperidine in excess of the equivalent amount under anhydrous conditions. The mixture is then preferably heated from about 25°C. to the reflux temperature for a period of from 1 hour to several days. A preferable reaction mixture is one which employs potassium-t-butoxide dissolved in t-butanol or an inert solvent such as ethyl ether or dioxan. The reaction may also be effected in the presence of piperidine and a strong base such as an alkali metal alkyl, e.g., butyl lithium, phenyl lithium, and the like in an inert solvent such as benzene or in excess piperidine acting as solvent as well as reactant. The resulting enamine product D is present in the reaction mixture and is conveniently recovered by partitioning between an aromatic hydrocarbon, e.g., benzene, toluene, or xylene, ethers and water. The resulting benzene extract of enamine is evaporated which leaves the product as a residue.

The enamine product is then converted by acidic hydrolysis to the desired biologically active product, 1-alkyl-4-(10,11-dihydro-10-oxo-dibenzo[a,d]cyclohepten-5-ylidene)piperidine which is further converted by lithium aluminum hydride or $NaBH_4$ or other metal hydride reducing agents to the corresponding 1-alkyl-4-(10,11-dihydro-10-hydroxy-dibenzo[a,d]cyclohepten-5-ylidene)piperidine. The 1-alkyl-4-(10,11-dihydro-10-(oxo- or hydroxy)-dibenzo[a,d]cyclohepten-5-ylidene)piperidine is then converted to the corresponding 1-alkenyl, e.g., allyl or methallyl piperidine, by dealkylation in conventional manner to produce the corresponding N-dealkylated compound followed by treatment of the dealkylated piperidine with a stoichiometrically equivalent amount of an alkenyl halide as, for example, allyl or methallyl bromide.

The 10- or 11-keto compounds E of my invention, containing a benzylmercapto substituent as the X and/or X' substituent, are converted by conventional means to the corresponding 10- or 11-ethylene ketal. The resulting compound is then converted to the corresponding mercapto compound by reduction with sodium in liquid ammonia followed by acid hydrolysis to regenerate the 10- or 11-keto compound E having a mercapto substituent as the X or X' substituent.

In the following illustrative examples, the isolation procedures are modified depending on product properties in accordance with principles well known to any skilled chemist.

EXAMPLE 1

1-Methyl-4-(5H-dibenzo[a,d]cyclohepten-5-ylidene)-piperidine hydrobromide

1-Methyl-4-(5H-dibenzo[a,d]cyclohepten-5-ylidene)piperidine hydrochloride, 50 g. (0.146 mole) is stirred while warming with 100 ml. of 20% NaOH solution and 200 ml. of benzene until all of the salt is converted to the base and base dissolved in the benzene layer. The benzene layer containing the product is separated, washed, dried and evaporated under reduced pressure leaving the free base as a residue, which is dissolved in 500 ml. of ether. Dry hydrogen bromide gas is bubbled into the ether solution slowly with rapid stirring until no more precipitate is formed. This salt is collected and dried in a vacuum oven at 60° for 24 hours to give 1-methyl-4-(5H-dibenzo[a,d]cyclohepten-5-ylidene)piperidine hydrobromide, m.p. 257°–258°C.

EXAMPLE 2

1-Methyl-4-(10,11-dibromo-10,11-dihydro-5H-dibenzo[a,d]cyclohepten-5-ylidene)piperidine hydrobromide 1-Methyl-4-(5H-dibenzo[a,d]cyclohepten-5-ylidene)piperidine hydrobromide, 18.40 g. (0.05 mole) is dissolved with warming in 750 ml. of glacial acetic acid. This solution is cooled to room temperature and 8.0 g., 2.6 ml., (0.05 mole) of bromine dissolved in 75 ml. of glacial acetic acid is added dropwise with stirring. After completion of the addition the mixture is stirred overnight. The crystals are collected, washed with a small amount of cold glacial acetic acid, then with dry ether, and then dried for 2 hours in a vacuum oven at 70° to give 1-methyl-4-(10,11-dibromo-10,11-dihydro-5H-dibenzo[a,d]cyclohepten-5-ylidene)-piperidine hydrobromide. Recrystallization from acetonitrile gives an analytical sample, m.p. 185°–186°C.

Anal. Calcd. for $C_{21}H_{21}NBr_2 \cdot HBr$: C, 47.75; H, 4.20; N, 2.65. Found: C, 47.80; H, 4.21; N, 2.61.

EXAMPLE 3

The procedure of Example 2 is repeated using a stoichiometrically equivalent amount of each of the following correspondingly substituted 1-methyl-4-(5H-dibenzo[a,d]cyclohepten-5-ylidene)piperidines having the following structure:

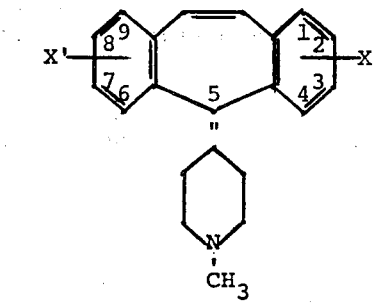

in which one or more of the hydrogens of the benzene rings is substituted by an X or an X' substituent as defined in the following table with resultant production of the corresponding 10,11-dibromo compound.

|  | X | X' |
|---|---|---|
| Compound (1) | 3-Trifluoromethyl | H |
| Compound (2) | 3-Phenyl | H |
| Compound (3) | 1-Phenyl | H |
| Compound (4) | 2-Phenyl | H |
| Compound (5) | 3-Phenyl | 7-Phenyl |
| Compound (6) | 1-Acetyl | H |
| Compound (7) | 2-Acetyl | H |
| Compound (8) | 3-Propionyl | H |
| Compound (9) | 2-Butyryl | H |
| Compound (10) | 3-Trifluoroacetyl | H |
| Compound (11) | 2-Amino | H |
| Compound (12) | 3-Amino | H |
| Compound (13) | 3-(N-methylamino) | H |
| Compound (14) | 1-(N-ethylamino) | H |
| Compound (15) | 2-(i-propylamino) | H |
| Compound (16) | 3-Diethylamino | H |
| Compound (17) | 1-Dimethylamino | H |
| Compound (18) | 3-Diisopropylamino | H |
| Compound (19) | 2-(N-Dibutyrylamino) | H |
| Compound (20) | 3-Acetamido | H |
| Compound (21) | 2-Propionamido | H |
| Compound (22) | 3-Butyramido | H |
| Compound (23) | 3-Trifluoroacetamido | H |
| Compound (24) | 3-Methylsulfonylamino | H |
| Compound (25) | 3-Ethylsulfonylamino | H |
| Compound (26) | 3-Chloro | H |
| Compound (27) | 2-Chloro | H |
| Compound (28) | 3-Chloro | 7-Chloro |
| Compound (29) | 1-Chloro | H |
| Compound (30) | 2-Bromo | H |
| Compound (31) | 3-Fluoro | H |
| Compound (32) | 1-Bromo | H |
| Compound (33) | 3-Bromo | H |
| Compound (34) | 3-Iodo | H |
| Compound (35) | 3-Methoxy | 7-Methoxy |
| Compound (36) | 3-Methoxy | H |
| Compound (37) | 1-Methoxy | H |
| Compound (38) | 1-Bromo | 7-Methoxy |
| Compound (39) | 1-Ethoxy | H |
| Compound (40) | 2-Propoxy | H |
| Compound (41) | 3-Butoxy | H |
| Compound (42) | 3-Trifluoromethoxy | H |
| Compound (43) | 1-Cyano | H |
| Compound (44) | 3-Cyano | H |
| Compound (45) | 2-Cyano | H |
| Compound (46) | 3-Carboxy | H |
| Compound (47) | 2-Carboxy | H |
| Compound (48) | 1-Carboxy | H |
| Compound (49) | 3-Carbamoyl | H |
| Compound (50) | 3-Methylcarbamoyl | H |
| Compound (51) | 3-Ethylcarbamoyl | H |
| Compound (52) | 1-Methyl | H |
| Compound (53) | 2-Methyl | H |
| Compound (54) | 3-Methyl | H |
| Compound (55) | 3-Methyl | 7-Methyl |
| Compound (56) | 3-(N,N-diethylcarbamoyl) | H |
| Compound (57) | 3-(N,N-dimethylcarbamoyl) | H |
| Compound (58) | 3-(N,N-dipropylcarbamoyl) | H |
| Compound (59) | 2-Carboethoxy | H |
| Compound (60) | 3-Carbomethoxy | H |
| Compound (61) | 1-Carbopropoxy | H |
| Compound (62) | 1-Benzylmercapto | H |
| Compound (63) | 2-Ethylmercapto | H |
| Compound (64) | 3-Methylmercapto | H |
| Compound (65) | 3-Methylmercapto-6-methylmercapto | H |
| Compound (66) | 3-Trifluoromethylmercapto | H |
| Compound (67) | 3-Methylsulfonyl | H |
| Compound (68) | 2-Ethylsulfonyl | H |
| Compound (69) | 1-N-butylsulfonyl | H |
| Compound (70) | 3-Trifluoromethylsulfonyl | H |
| Compound (71) | 3-Sulfamoyl | H |
| Compound (72) | 3-(N-methylsulfamoyl) | H |
| Compound (73) | 3-(N-ethylsulfamoyl) | H |
| Compound (74) | 3-(N,N-dimethylsulfamoyl) | H |
| Compound (75) | 3-(N,N-diethylsulfamoyl) | H |
| Compound (76) | 3-Phenyl | 7-(p-Tolyl) |
| Compound (77) | 2-Phenyl | 8-(p-Methoxyphenyl) |
| Compound (78) | 2-Acetyl | 7-Methyl |
| Compound (79) | 1-Methyl | 7-Methyl |
| Compound (80) | 1-Ethyl | 8-Ethyl |
| Compound (81) | 3-Ethyl | 9-Ethyl |
| Compound (82) | 3-Propyl | 7-Ethyl |

EXAMPLE 4

The procedure of Example 3 is repeated using a compound in which the N-methyl-piperidine substituent is replaced in each and every instance by each of the following substituents:

(1) 1,2-dimethyl-piperidine
(2) 1,2-diethyl-piperidine (3) 1,3-dimethyl-piperidine
(4) 1,2,2-trimethyl-piperidine
(5) 1,2,5-trimethyl-piperidine
(6) 1,2,6-trimethyl-piperidine
(7) 1-ethyl-2-methyl-piperidine cycloheptene compound.
(8) 1,2-diethyl-piperidine
(9) 1-ethyl-3-methyl-piperidine
(10) 1-ethyl-2,2-dimethyl-piperidine
(11) 1-ethyl-2,5-dimethyl-piperidine
(12) 1-ethyl-2,6-dimethyl-piperidine

EXAMPLE 5

1-Methyl-4-(10-bromo-5H-dibenzo[a,d]cyclohepten-5-ylidene)piperidine

To 600 ml. of a 0.40 M (0.24 mole) solution of potassium t-butoxide in t-butanol is added 42.1 g. (0.079 mole) of 1-methyl-4-(10,11-dibromo-10,11-dihydro-5H-dibenzo[a,d]cyclohepten-5-ylidene)piperidine hydrobromide and the mixture stirred vigorously under anhydrous conditions for 6 hours at room temperature. The reaction mixture is poured into 2 L. of water and extracted 3 times with 100 ml. each of benzene. The combined benzene extracts are dried over anhydrous $MgSO_4$, filtered, the $MgSO_4$ washed with benzene, and the benzene solution evaporated to dryness on a rotary evaporator. There remains 27.9 g. of crystalline product. This product is recrystallized by dissolving in 750 ml. of boiling hexane, filtered hot, the volume reduced to 200 ml. by boiling off hexane, seeding and allowing to crystallize. The crystals are collected and dried in a vacuum oven at 60° overnight to give 1-methyl-4-(10-bromo-5H-dibenzo[a,d]cyclohepten-5-ylidene)piperidine, m.p. 127°–129°C. Three more recrystallizations from hexane gives an analytical sample with m.p. 130°–131°C.

Anal. Calcd. for $C_{21}H_{20}BrN$: C, 68.85; H, 5.69; N, 3.82; Br, 21.82. Found: C, 68.78, H, 5.45; N, 3.79; Br, 21.94.

EXAMPLE 6

The procedure of Example 5 is repeated using as starting materials each of the products obtained in accordance with the procedure of Examples 3 and 4, respectively, to produce the corresponding mono bromo dibenzocycloheptene compound.

EXAMPLE 7

1-Methyl-4-(10-(1-piperidyl)-5H-dibenzo[a,d]cyclohepten-5-ylidene)piperidine

1-Methyl-4-(10-bromo-5H-dibenzo[a,d]cyclohepten-5-ylidene)piperidine, 2.87 g. (0.0079 mole), 50 ml. of a 0.4M solution of potassium t-butoxide in t-butanol, and 20 ml. of dry piperidine is stirred and refluxed under anhydrous conditions for 6 hours. The reaction mixture is cooled and partitioned between 350 ml. of benzene and 50 ml. of water. The benzene layer is then extracted 5 more times with 50 ml. each of water. The benzene layer is then dried over anhydrous $MgSO_4$, filtered, and the benzene evaporated. This gives a single spot on t.l.c. and is used directly in the next step.

The product is crystallized from acetonitrile-methanol mixture. A sample sublimed for analysis has a m.p. of 71.5°–78°C.

Anal. Calcd. for $C_{26}H_{30}N_2$: C, 84.28; H, 8.16; N, 7.56. Found: C, 83.85; H, 8.14; N, 7.50.

EXAMPLE 8

The procedure of Example 7 is repeated using as starting materials each of the products obtained according to Example 6 with resultant production of the corresponding 10-(1-piperidyl)-5H-dibenzo[a,d]cycloheptene compound.

EXAMPLE 9

1-Methyl-4-(10,11-dihydro-10-oxo-dibenzo[a,d]cyclohepten-5-ylidene)piperidine

1-Methyl-4-(10-(1-piperidyl)-5H-dibenzo[a,d]cyclohepten-5-ylidene)piperidine, 2.4 g., is refluxed for 4 hours with 100 ml. of 10% HCl in water and 50 ml. of methanol. The methanol is evaporated and the remaining oil and water is made basic with solid $NaHCO_3$ until no more $CO_2$ is evolved. It is then extracted 3 times with 50 ml. each of toluene, combined extracts dried over $MgSO_4$, filtered, and the toluene evaporated on a rotary evaporator leaving a residual product which crystallizes on standing. Three recrystallizations of this product from hexane gives 1-methyl-4-(10,11-dihydro-10-oxo-dibenzo[a,d]cyclohepten-5-ylidene)piperidine, m.p. 142°–143°C.

Anal. Calcd. for $C_{21}H_{21}NO$: C, 83.13; H, 6.98; N, 4.62. Found: C, 82.96; H, 6.80; N, 4.72.

EXAMPLE 10

The procedure of Example 9 is repeated using as the starting materials each of the products obtained in accordance with Example 8 with resultant production of the corresponding 10,11-dihydro-10-oxo-dibenzo[a,d]cycloheptene compound.

EXAMPLE 11

1-Methyl-4-(10,11-dihydro-10-oxo-dibenzo[a,d]cyclohepten-5-ylidene)piperidine

EXAMPLE 11

1Methyl-4-(10,11-dihydro-10-oxo-dibenzo[a,d]cyclohepten-5-ylidene)piperidine

1-Methyl-4-(10-bromo-5H-dibenzo[a,d]cyclohepten-5-ylidene)piperidine, 7.32 g. (0.02 mole) is dissolved in 100 ml. of dry piperidine. To this solution is added slowly 25 ml. of a 1.6M solution of butyl lithium in hexane (0.04 mole) under anhydrous conditions and then stirred and refluxed for 8 hours under anhydrous conditions. The reaction is cooled and poured into 500 ml. of benzene and extracted 6 times with 100 ml. of water. The benzene is dried over anhydrous $MgSO_4$, filtered, and the benzene removed on a rotary evaporator leaving 1-methyl-4-(10-(1-piperidyl)-5H-dibenzo[a,d]cyclohepten-5-ylidene)piperidine as an oil which still has some solvent in it.

This enamine product is then hydrolyzed by refluxing with stirring in 150 ml. 10% HCl in water and 75 ml. of methanol. The methanol is then removed by evaporation of the reaction mixture on a rotary evaporator. The residual material containing the desired product is made alkaline by adding solid $NaHCO_3$ until no more $CO_2$ is evolved. The residue is then extracted with toluene and ether. The combined extracts containing the product are dried over anhydrous $MgSO_4$, filtered, and the solvents removed with a rotary evaporator. There remains a dark brown residual oil which when seeded crystallizes slowly. This product is collected and recrystallized from hexane two times to give 1-methyl-4-

(10,11-dihydro-10-oxo-dibenzo[a,d]cyclohepten-5-ylidene)piperidine, m.p. 138°–140°C. Three more recrystallizations from hexane gives product, m.p. 141°–142°C.

Anal. Calcd. for $C_{21}H_{21}NO$: N, 4.62. Found: N, 4.78.

EXAMPLE 12

1-Methyl-4-(10,11-dihydro-10-hydroxy-5H-dibenzo[a,d]cyclohepten-5-ylidene)piperidine A solution of 3.0 g. (0.01 mole) of 1-methyl-4-(10,11-dihydro-10-oxo-5H-dibenzo[a,d]cyclohepten-5-ylidene)piperidine (0.01 mole) in 200 ml. of dry ether is added dropwise in a dry inert atmosphere to a stirred suspension of 3.8 g. (0.1 mole) of lithium aluminum hydride. The reaction is then stirred overnight (20 hours) at room temperature under a dry inert atmosphere. Then there is added dropwise carefully with stirring 3 ml. of water followed by 3 ml. of 20% NaOH solution in water followed by 15 ml. of water. The ether solution of the product is decanted and the remaining salts washed with ether and decanted. The combined ether solutions of the product are dried over anhydrous $MgSO_4$, filtered, and the ether evaporated on a rotary evaporator. This gives after one recrystallization from ethanol 1-methyl-4-(10,11-dihydro-10-hydroxy-5H-dibenzo[a,d]cyclohepten-5-ylidene)piperidine, m.p. 205°–206°C.

Anal. Calcd. for $C_{21}H_{23}NO$: C, 82.58; H, 7.59; N, 4.59. Found: C, 82.18; H, 7.77; N, 4.62.

EXAMPLE 13

1-Methyl-4-(10,11-dihydro-10-hydroxy-5H-dibenzo[a,d]cyclohepten-5-ylidene)piperidine A solution of 0.95 g. (0.025 mole) of sodium borohydride and 5 drops of 10% sodium hydroxide solution is added dropwise to a stirred solution of 1.5 g. (0.005 mole) of 1-methyl-4-(10,11-dihydro-10-oxo-5H-dibenzo[a,d]cyclohepten-5-ylidene)piperidine. After about 4 ml. of the sodium borohydride solution is added the product begins to crystallize from the reaction. Upon completion of the addition, the mixture is cooled and stirred in an ice bath and the product is filtered, washed with 50% methanol in water and dried overnight in a vacuum oven at 80°C. to give 0.94 g. of 1-methyl-4-(10,11-dihydro-10-hydroxy-5H-dibenzo[a,d]cyclohepten-5-ylidene)piperidine, m.p. 206°–207°C.

EXAMPLE 14

Representative Pharmaceutical Composition Preparation

A typical tablet containing 1 mg. of 1-methyl-4(10,11-dihydro-10-oxo-dibenzo[a,d]cycloheptene-5-ylidene)piperidine per tablet is prepared by mixing together with the active ingredient calcium phosphate dibasic, lactose and starch in the amounts shown in the table below. After these ingredients are thoroughly mixed the appropriate amount of magnesium stearate is added and the dry mixture blended for an additional three minutes. This mixture is then compressed into tablets weighing approximately 124 mgs. each.

| Tablet Formula | Mgs. Per Tablet |
|---|---|
| 1-Methyl-4-(10,11-dihydro-10-oxo-dibenzo[a,d]cycloheptene-5-ylidene)-piperidine | 1 |
| Calcium phosphate dibasic | 52 |
| Lactose | 60 |
| Starch | 10 |
| Magnesium stearate | 1 |
| Total | 124 |

Capsules for oral use each containing 1 mg. of 1-methyl-4-(10,11-dihydro-10-oxo-dibenzo[a,d]cycloheptene-5-ylidene)piperidine are prepared by blending 1 gram of 1-methyl-4-(10,11-dihydro-10-oxo-dibenzo[a,d]cycloheptene-5-ylidene)piperidine with 287 grams of lactose, U.S.P. 4.1 grams of magnesium stearate. This is then used to fill 1,000 capsules each containing 1 mg. of 1-methyl-4-(10,11-dihydro-10-oxo-dibenzo[a,d]cycloheptene-5-ylidene)piperidine.

Similar compositions are prepared utilizing as the active ingredient the products prepared according to Examples 9, 10, 11 and 12.

What is claimed:

1. A compound of the formula

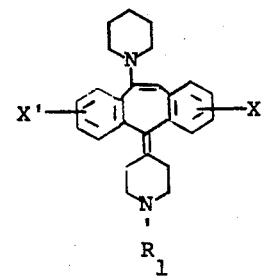

wherein
$R_1$ is lower alkyl;
X and X' are similar or dissimilar and are selected from hydrogen,
an alkyl group having up to 6 carbon atoms,
a perfluoroalkyl group having up to 4 carbon atoms,
phenyl amino,
an alkylamino group having up to 4 carbon atoms,
a dialkylamino group having up to 8 carbon atoms,
an alkylsulfonylamino group having up to 4 carbon atoms, halogen (fluorine, chlorine, bromine or iodine), hydroxyl,
an alkoxy group having up to 4 carbon atoms,
a perfluoroalkoxyl group having up to 4 carbon atoms,
cyano,
carboxy,
carbamoyl,
an alkylcarbamoyl group having up to 5 carbon atoms,
a dialkylcarbamoyl group having up to 9 carbon atoms,
a carbalkoxy group having up to 6 carbon atoms,
an alkylmercapto group having up to 4 carbon atoms,
a perfluoroalkylmercapto group having up to 4 carbon atoms,
an alkylsulfonyl group having up to 4 carbon atoms, a perfluoroalkylsulfonyl group having up to 4 carbon atoms, sulfamoyl,
an alkylsulfamoyl group having up to 4 carbon atoms,
or a dialkylsulfamoyl group having up to 8 carbon atoms.
2. A compound of the formula
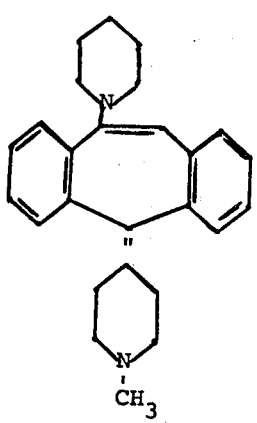
* * * * *